United States Patent
Najafi et al.

(10) Patent No.: US 8,343,068 B2
(45) Date of Patent: Jan. 1, 2013

(54) SENSOR UNIT AND PROCEDURE FOR MONITORING INTRACRANIAL PHYSIOLOGICAL PROPERTIES

(75) Inventors: Nader Najafi, Ann Arbor, MI (US); Catherine Hook Morgan, Ann Arbor, MI (US); David Joseph Goetzinger, Livonia, MI (US); Sonbol Massoud-Ansari, El Dorado Hills, CA (US)

(73) Assignee: Integrated Sensing Systems Inc., Ypsilanti, MI (US)

( * ) Notice: Subject to any disclaimer, the term of this patent is extended or adjusted under 35 U.S.C. 154(b) by 0 days.

(21) Appl. No.: 12/786,685

(22) Filed: May 25, 2010

(65) Prior Publication Data

US 2010/0262036 A1  Oct. 14, 2010

Related U.S. Application Data

(63) Continuation-in-part of application No. 12/325,502, filed on Dec. 1, 2008, now abandoned.

(60) Provisional application No. 61/004,508, filed on Nov. 29, 2007, provisional application No. 61/008,202, filed on Dec. 19, 2007.

(51) Int. Cl.
*A61B 5/00* (2006.01)

(52) U.S. Cl. ............................................. 600/561

(58) Field of Classification Search ............... 600/378, 600/561, 302, 587
See application file for complete search history.

(56) References Cited

U.S. PATENT DOCUMENTS

| | | | | |
|---|---|---|---|---|
| 5,054,497 | A * | 10/1991 | Kapp et al. | 600/561 |
| 6,673,022 | B1 * | 1/2004 | Bobo et al. | 600/561 |
| 7,785,268 | B2 * | 8/2010 | Miethke et al. | 600/561 |
| 2002/0052563 | A1 * | 5/2002 | Penn et al. | 600/561 |
| 2002/0151770 | A1 * | 10/2002 | Noll et al. | 600/300 |
| 2006/0020224 | A1 * | 1/2006 | Geiger | 600/561 |
| 2008/0139959 | A1 * | 6/2008 | Miethke et al. | 600/561 |
| 2009/0005701 | A1 * | 1/2009 | Dextradeur et al. | 600/549 |

* cited by examiner

*Primary Examiner* — Max Hindenburg
(74) *Attorney, Agent, or Firm* — Hartman Global IP Law; Gary M. Hartman; Domenica N. S. Hartman

(57) ABSTRACT

An anchor for an implantable sensing device, a sensor unit formed by the anchor and sensing device, and a surgical procedure for implanting the sensor unit for monitoring a physiological parameter within a cavity of a living body, such as an intracranial physiological property. The anchor includes a shank portion and a head portion. The shank portion defines a distal end of the anchor and has a bore defining an opening at the distal end. The head portion defines a proximal end of the anchor and has a larger cross-sectional dimension than the shank portion. The sensor unit comprises the anchor and the sensing device placed and secured within the bore of the anchor so that a sensing element of the sensing device is exposed for sensing the physiological parameter within the cavity.

46 Claims, 5 Drawing Sheets ary of the invention

SENSOR UNIT AND PROCEDURE FOR MONITORING INTRACRANIAL PHYSIOLOGICAL PROPERTIES

CROSS REFERENCE TO RELATED APPLICATIONS

This application is a continuation-in-part application of U.S. patent application Ser. No. 12/325,502, which claims the benefit of U.S. Provisional Application Nos. 61/004,508 filed Nov. 29, 2007, and 61/008,202 filed Dec. 19, 2007. The contents of these prior patent applications are incorporated herein by reference.

BACKGROUND OF THE INVENTION

The present invention generally relates to implantable medical devices, monitoring systems and associated procedures. More particularly, this invention relates to a sensor unit comprising an anchor and an implantable medical sensing device, and to a procedure for implanting the sensing device for monitoring intracranial physiological properties.

Wireless devices such as pressure sensors have been implanted and used to monitor heart, brain, bladder and ocular function. With this technology, capacitive pressure sensors are often used, by which changes in pressure cause a corresponding change in the capacitance of an implanted capacitor (tuning capacitor). The change in capacitance can be sensed, for example, by sensing a change in the resonant frequency of a tank or other circuit coupled to the implanted capacitor.

Telemetric implantable sensors that have been proposed include batteryless pressure sensors developed by CardioMEMS, Inc., Remon Medical, and the assignee of the present invention, Integrated Sensing Systems, Inc. (ISSYS). For example, see commonly-assigned U.S. Pat. Nos. 6,926,670 and 6,968,734 to Rich et al., and N. Najafi and A. Ludomirsky, "Initial Animal Studies of a Wireless, Batteryless, MEMS Implant for Cardiovascular Applications," Biomedical Microdevices, 6:1, p. 61-65 (2004). With such technologies, pressure changes are typically sensed with an implant equipped with a mechanical (tuning) capacitor having a fixed electrode and a moving electrode, for example, on a diaphragm that deflects in response to pressure changes. The implant is further equipped with an inductor in the form of a fixed coil that serves as an antenna for the implant, such that the implant is able to receive a radio frequency (RF) signal transmitted from outside the patient to power the circuit, and also transmit the resonant frequency as an output of the circuit that can be sensed by a reader outside the patient. The implant can be placed with a catheter, for example, directly within the heart chamber whose pressure is to be monitored, or in an intermediary structure, for example, the atrial or ventricular septum of the heart.

Presently in the United States, roughly one million people are treated for head injuries each year, with over a quarter million of these being moderate or severe injuries. Traumatic brain injuries currently account for approximately 70,000 deaths each year in the United States, with an additional 80,000 patients having severe long-term disabilities. Monitoring intracranial pressure (ICP) to identify intracranial hypertension (ICH) is one of the most important steps in treatment of severe head injuries. The ability to accurately monitor and identify high ICP levels enables physicians to diagnose and treat the underlying causes and significantly reduce the morbidity and mortality rates of these patients.

ICP is currently measured and recorded through a variety of systems, such as intraventricular catheters, subarachnoid bolts, and catheter tip strain gauges. However, each of these systems has significant drawbacks, including the need for repositioning and balancing, the occurrence of occlusions and blockages, and the risk of infection.

BRIEF SUMMARY OF THE INVENTION

The present invention provides an anchor for an implantable sensing device, a sensor unit formed by the anchor and sensing device, and a surgical procedure for implanting the sensor unit for monitoring a physiological parameter within a cavity of a living body, such as an intracranial physiological property.

The anchor includes a shank portion and a head portion. The shank portion defines a distal end of the anchor and has a bore defining an opening at the distal end. The head portion defines a proximal end of the anchor and has a larger cross-sectional dimension than the shank portion. The sensor unit is configured to position a sensing element for monitoring a physiological parameter within a cavity of a living body, and includes the anchor and a sensing device that comprises the sensing element and is configured to be placed and secured within the bore of the anchor.

The surgical procedure generally entails assembling the sensor unit by placing the sensing device within the bore of the anchor so that the sensing element of the sensing device is exposed at the distal end of the anchor for sensing a physiological parameter. An incision is made in the scalp of a patient to expose a portion of the skull, a hole is made through the skull, and the sensor unit is placed in the hole such that the distal end of the sensor unit (as defined by the sensing device or the distal end of the anchor) is flush with or protrudes into the cranial cavity within the skull, while an oppositely-disposed proximal end of the sensor unit (as defined by the proximal end of the anchor) remains outside the skull. The anchor is secured to the skull so that the hole in the skull is occluded by the sensor unit. A readout device located outside the patient can be used to telemetrically communicate with the sensing device to obtain a reading of the physiological parameter sensed by the sensing element.

The sensor unit and implantation procedure are intended to be particularly well suited for providing safe, fast, detailed, real-time, and continuous intracranial pressure measurements. Compared to existing systems used for ICP monitoring, particular advantages of the invention include a miniature wireless unit with an uncomplicated anchoring system and implantation/placement procedure that enables accurate placement of a sensing element at various depths in the cranial cavity. The invention also offers reduced infection risk and patient discomfort, increased patient mobility, and improved post-surgical patient care. Preferred embodiments of the sensor unit are very small, allowing the unit to be easily placed under the scalp with minimal discomfort to the patient.

Other objects and advantages of this invention will be better appreciated from the following detailed description.

BRIEF DESCRIPTION OF THE DRAWINGS

FIG. 4 represents a perspective view of a cylindrical self-contained sensing device of the type represented in FIG. 2a.

DETAILED DESCRIPTION OF THE INVENTION

FIGS. 1a through 4 schematically illustrate monitoring systems and components thereof that implement one or more implantable sensing devices (10,30,60) adapted to be placed through a hole in the skull of a patient for monitoring one or more intracranial physiological parameters, a notable but nonlimiting example of which is intracranial pressure (ICP). Each monitoring system preferably makes use of a readout unit (20,50,80) adapted to wirelessly communicate with the sensing device. The sensing device is placed at a desired location within the skull with an anchor 120, of which several embodiments are shown in FIGS. 5 through 8. Together, the sensing device and its anchor 120 define a sensor unit 150. Because the sensing device communicates wirelessly with a readout unit, the sensor unit 150 lacks a wire, cable, tether, or other physical component that conducts the output of the sensing device to the readout unit or another processing or transmission device outside the body of a patient. As such, the sensor unit 150 defines the only implanted portion of the monitoring system.

Figure 1A:
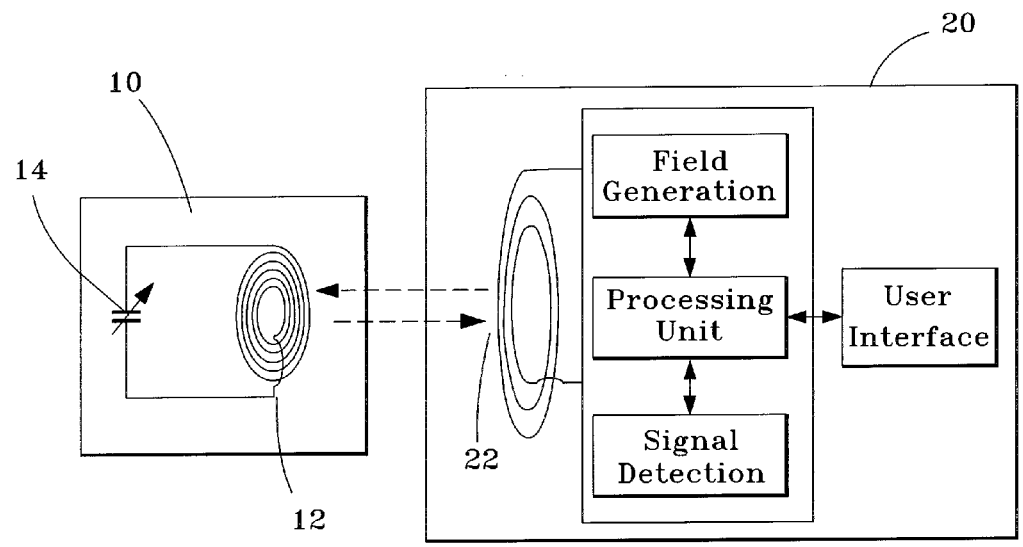
FIGS. 1a and 1b are block diagrams of wireless pressure monitoring systems that utilize resonant and passive sensing schemes, respectively, which can be utilized by the present invention.
Figure 1B:
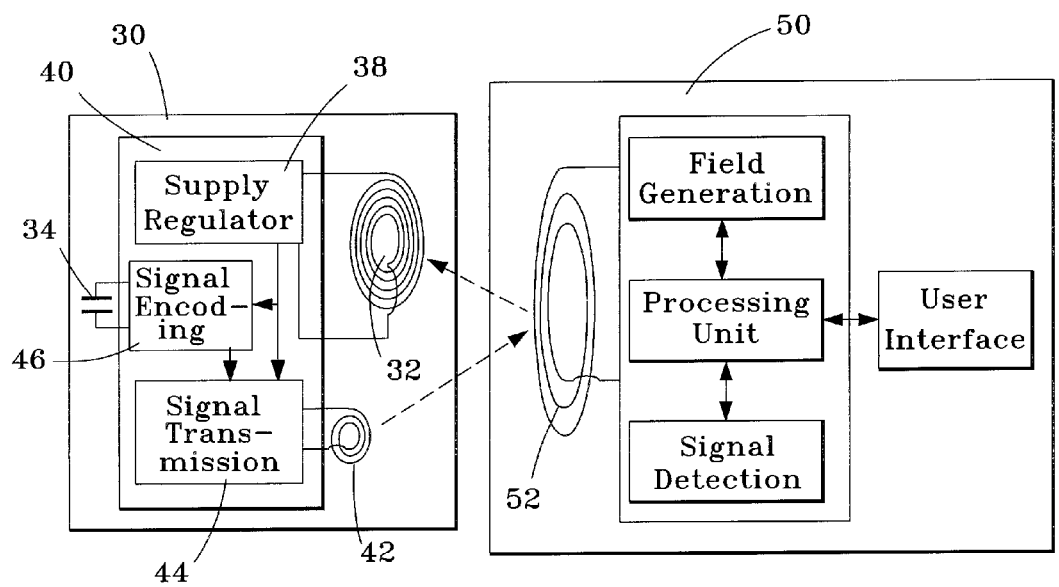

FIGS. 1a and 1b represent two types of wireless pressure sensing schemes disclosed in U.S. Pat. Nos. 6,926,670 and 6,968,734 to Rich et al., and capable of use with the present invention. In FIG. 1a, an implant 10 is shown as operating in combination with a non-implanted external reader unit 20, between which a wireless telemetry link is established using a resonant scheme. The implant 10 contains a packaged inductor coil 12 and a pressure sensor in the form of a mechanical capacitor 14. Together, the inductor coil 12 and capacitor 14 form an LC (inductor-capacitor) tank resonator circuit that has a specific resonant frequency, expressed as $1/(LC)^{1/2}$, which can be detected from the impedance of the circuit. At the resonant frequency, the circuit presents a measurable change in magnetically-coupled impedance load to an external coil 22 associated with the reader unit 20. Because the resonant frequency is a function of the capacitance of the capacitor 14, the resonant frequency of the LC circuit changes in response to pressure changes that alter the capacitance of the capacitor 14. Based on the coil 12 being fixed and therefore having a fixed inductance value, the reader unit 20 is able to determine the pressure sensed by the implant 10 by monitoring the resonant frequency of the circuit.

FIG. 1b shows another wireless pressure sensor implant 30 operating in combination with a non-implanted external reader unit 50. A wireless telemetry link is established between the implant 30 and reader unit 50 using a passive, magnetically-coupled scheme, in which onboard circuitry of the implant 30 receives power from the reader unit 50. In the absence of the reader unit 50, the implant 30 lays passive and without any internal means to power itself. When a pressure reading is desired, the reader unit 50 must be brought within range of the implant 30. The implant 30 contains a packaged inductor coil 32 and a pressure sensor in the form of a mechanical capacitor 34. The reader unit 50 has a coil 52 by which an alternating electromagnetic field is transmitted to the coil 32 of the implant 30 to induce a voltage in the implant 30. When sufficient voltage has been induced in the implant 30, a rectification circuit 38 converts the alternating voltage on the coil 32 into a direct voltage that can be used by electronics 40 as a power supply for signal conversion and communication. At this point the implant 30 can be considered alert and ready for commands from the reader unit 50. The implant 30 may employ the coil 32 as an antenna for both reception and transmission, or it may utilize the coil 32 solely for receiving power from the reader unit 50 and employ a second coil 42 for transmitting signals to the reader unit 50. Signal transmission circuitry 44 receives an encoded signal generated by signal conditioning circuitry 46 based on the output of the capacitor 34, and then generates an alternating electromagnetic field that is propagated to the reader unit 50 with the coil 42. The implant 30 is shown in FIG. 1b without a battery, and therefore its operation does not require occasional replacement or charging of a battery. Instead, the energy required to perform the sensing operation is entirely derived from the reader unit 50. However, the implant 30 of FIG. 1b could be modified to use a battery or other power storage device to power the implant 30 when the reader unit 50 is not sufficiently close to induce a voltage in the implant 30.

Figure 2A:
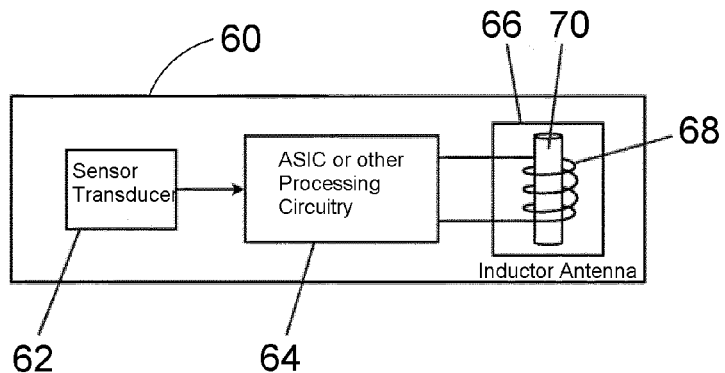
FIGS. 2a and 2b are schematic representations of a wireless sensing device and a readout device suitable for use in wireless monitoring systems of this invention.
Figure 2B:
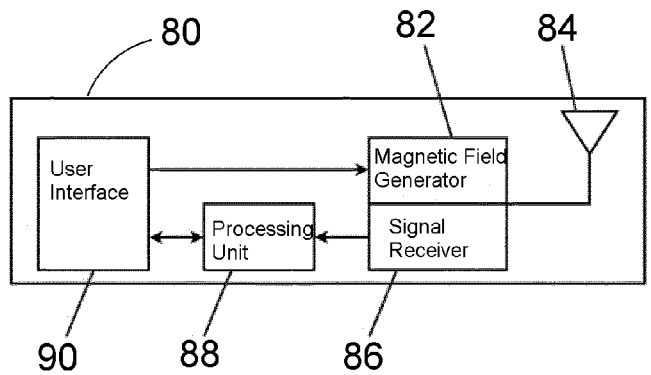

While the resonant and passive schemes described in reference to FIGS. 1a and 1b are within the scope of the invention, FIG. 2a represents a more preferred sensing device 60 that translates a physiologic parameter into a frequency tone and modulates the impedance of an antenna with the frequency tone to communicate the physiologic parameter to an external readout unit 80 (FIG. 2b). FIG. 2a represents the wireless implantable sensing device 60 as comprising a transducer 62, electronic circuitry 64 (e.g., an application-specific integrated circuit, or ASIC), and an antenna 66. The antenna 66 is shown as comprising windings 68 (e.g., copper, silver or gold wire) wrapped around a core 70 (e.g., ferrite), though other antenna configurations (for example, other three dimensional shapes) and materials are foreseeable. The transducer 62 is preferably a MEMS device, more particularly a micromachine fabricated by additive and subtractive processes performed on a substrate. The substrate can be rigid, flexible, or a combination of rigid and flexible materials. Notable examples of rigid substrate materials include glass, semiconductors, silicon, ceramics, carbides, metals, hard polymers, and TEFLON. Notable flexible substrate materials include various polymers such as parylene and silicone, or other biocompatible flexible materials. A particular but nonlimiting example of the transducer 62 is a MEMS capacitive pressure sensor for sensing pressure, such as intracranial pressure (ICP) of the cerebrospinal fluid, though other materials and any variety of sensing elements, e.g., capacitive, inductive, resistive, piezoelectric, etc., could be used. For example, the transducer 62 could be configured to sense temperature, flow, acceleration, vibration, pH, conductivity, dielectric constant, and chemical composition, including the composition and/or contents of cerebrospinal fluid. The sensing device 60 may be powered with a battery or other power storage device, but in preferred embodiments is powered entirely by the readout unit 80 schematically represented in FIG. 2b.

In addition to powering the sensing device 60, the readout unit 80 is represented as being configured to receive an output signal from the sensing device 60, process the signal, and relay the processed signal as data in a useful form to a user. The readout unit 80 is shown equipped with circuitry 82 that generates a high-frequency (e.g., 13.56 MHz), high-power signal for an antenna 84 to create the magnetic field needed in communicate with the sensing device 60. The readout unit 80 contains additional circuitry 86 to receive and demodulate a backscattered signal from the sensing device 60, which is then processed with a processing unit 88 using calibration coefficients to quantify the physiological parameter of interest. The readout unit 80 is further shown as equipped with a user interface 90, by which the operation of the readout unit 80 can be controlled to allow data logging or other user control and data examination. The readout unit 80 can be further configured for wireless or wired communication with a computer, telephone, or web-based system.

Figure 3:
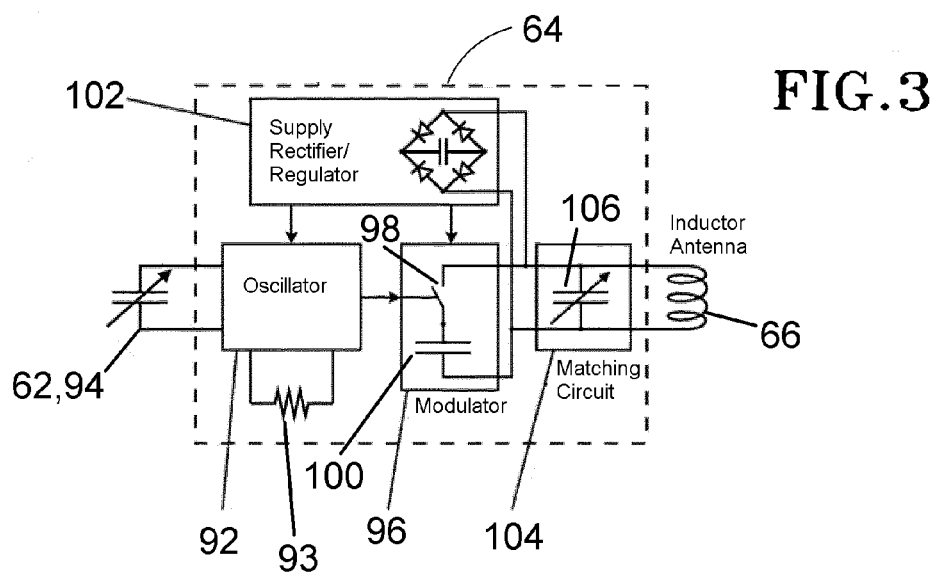
FIG. 3 is a circuit diagram representing a transducer, processing circuitry, and an antenna of a wireless sensing device in accordance with a particular embodiment of the invention.

FIG. 3 represents a block diagram showing particularly suitable components for the electronic circuitry 64 of FIG. 2a. The circuitry 64 includes an oscillator 92, for example a relaxation oscillator, connected to a resistor 93 and a MEMS mechanical capacitor 94 as an example of the transducer 62 of FIG. 2a. A preferred MEMS capacitor 94 comprises a fixed electrode and a moving electrode on a diaphragm that deflects relative to the fixed electrode in response to pressure, such that the capacitor 94 is able to serve as a pressure sensing element for the transducer 62. A nonlimiting example of a preferred MEMS capacitor 94 has a pressure range of about −100 to about +300 mmHg, with an accuracy of about 1 mmHg. Alternatively, a variable resistor transducer could be used with a fixed capacitance, or an inductor could be substituted for the transducer or fixed circuit element. Based on the RC or other time constant $(1/(LC)^{1/2}$, the oscillator 92 produces a frequency tone that directly relates to the capacitive value of the capacitor 94 and, therefore, the physiologic parameter of interest.

The circuitry 64 is further shown as including a modulator 96, with which the frequency tone of the oscillator 92 is encoded on a carrier frequency, placed on the antenna 66, and then transmitted to the readout unit 80. This is accomplished simply by opening and closing a switch 98 and adding a capacitance 100 to the antenna matching circuit, resulting in an AM (amplitude modulation) LSK (load shift keying) type modulation. This transmission approach is similar to that used in RFID (radio frequency identification) communications, except RFID does not typically encode analog information but instead encodes a few digital bits either on an AM LSK or FSK (frequency shift keying) modulation.

Because the preferred embodiment of the sensing device 60 does not utilize wires to transmit data or power to the readout unit 80 (or another remote device), nor contains an internal power source, the circuitry 64 further includes a regulator/rectifier 102 to extract its operating power from electromagnetic (EM) energy generated by the readout unit 80 or another EM power source. The regulator/rectifier 102 rectifies incoming power from the inductive antenna 66 and conditions it for the other circuit components within the circuitry 64. Finally, a matching circuit 104 is shown as comprising a trimmable capacitor bank 106 to resonate the inductor antenna 66, which is energized by the magnetic field and backscatters data as previously described.

As an alternative to the embodiment of FIG. 3, the modulator 96 could use a 13.56 MHz (or other frequency) magnetic field as a clock reference to create a second carrier frequency, such as one that is one-quarter or another sub-multiple or multiple of the original frequency. The second carrier frequency can then be amplitude modulated (AM) using the oscillator frequency tone and transmitted to the readout unit 80 via the same antenna 66. In this embodiment, the readout unit 80 may or may not have a second antenna to receive the second carrier frequency-based AM signal.

The communication scheme described above differs from resonate tank communication systems that use capacitive pressure transducer elements in conjunction with an inductor/antenna. In particular, the circuitry 64 allows the use of any frequency for the high power readout unit 80, which in preferred embodiments utilizes an industrial, scientific, medical (ISM) band frequency. In contrast, the frequencies and potentially large bandwidths required of resonate tank communication systems are subject to FCC emission limitations, likely requiring the use of extra shielding or potentially other measures taken in the facilities where the sensing device 60 and readout unit 80 are to be used. Another feature of the circuitry 64 is the allowance of more combinations of oscillator elements to be used. Because resonator tank systems require an inductive element and a capacitive element in which at least one of the elements serves as a transducer, resonator tank systems do not lend themselves well to resistive-based or other based sensors. Finally, the circuitry 64 also allows for signal conditioning, such as transducer compensation, which allows for such items as removing temperature dependence or other non-idealities that may be inherent to the transducer 62. In the embodiment of FIG. 3, a negative temperature coefficient of the MEMS capacitor 94 can be compensated with simple circuitry relying on the positive temperature coefficient of resistor elements arranged in a trimmable bank of two resistor units with largely different temperature coefficients that can be selectively added in a trimming procedure in production to select the precise level to compensate the transducer variation.

Restrictive levels of energy available to small implantable medical sensing devices and the desire to maximize data rates to capture more detailed physiological parameter response have typically been met with a robust type of analog communication that places information on the frequency rather than amplitude of the carrier. In U.S. Pat. No. 6,929,970 to Rich et al., a secondary carrier frequency is used for communication with an interrogator unit, resulting in a technique that consumes substantially more power in the implant and requires a second external antenna to receive the signal. The greater power consumption of the implant necessitates a tradeoff between smaller size and longer communication range. In contrast, the communication scheme described above in reference to FIGS. 2a, 2b and 3 draws upon the RFID-type communications, such as those described in U.S. Pat. Nos. 7,015,826 and 6,622,567, whose contents are incorporated herein by reference. However instead of communicating digital data using a fixed rate clock, the present invention transmits analog information as the frequency of the clock to lower power consumption and enhance powering and communication range. In this way, much of the readout unit 80 can utilize hardware that is commercially available for RFID, except that a different demodulator is required. An early example of RFID can be found in U.S. Pat. No. 4,333,072.

Capacitive sensors, including the capacitors 14 and 34 of FIGS. 1a and 1b and the preferred MEMS capacitor 94 of FIG. 3, have a high impedance output. Locating the associated electronics (for example, electronics 40 in FIG. 1b and electronic circuitry 64 in FIGS. 2a and 3) in close proximity to the MEMS capacitors 34 and 94 allows the conversion of the capacitor's high impedance output to a low impedance output. As a result, standard lead transfer methods can then be used to transfer this low-impedance signal. For this purpose, the electronics 40/64 and the MEMS capacitors 34/94 can be fabricated on the same substrate or fabricated separately and attached to a substrate, or in some cases, the electronics 40/64 can be directly mounted on the substrate in or on which the capacitor 34/94 has been fabricated. In all cases, the electronics 40/64 and the capacitor 34/94 are electrically connected together. At minimum, the implant 30 or device 60 contains the capacitor 34 or 94 and electronics 40 or 64 to define an assembly that can be inserted through the skull and secured in place using the anchor 120. As discussed below in reference to FIG. 9, this assembly may be a subassembly of the implant 30 or device 60, and can be connected to a second subassembly containing other components of the implant 30 or device 60, such as the coils 32 and 42 (FIG. 1b) or the antenna 66 (FIGS. 2a and 3) and optionally other electronics components, inductor coils, battery, etc.

Figure 4:
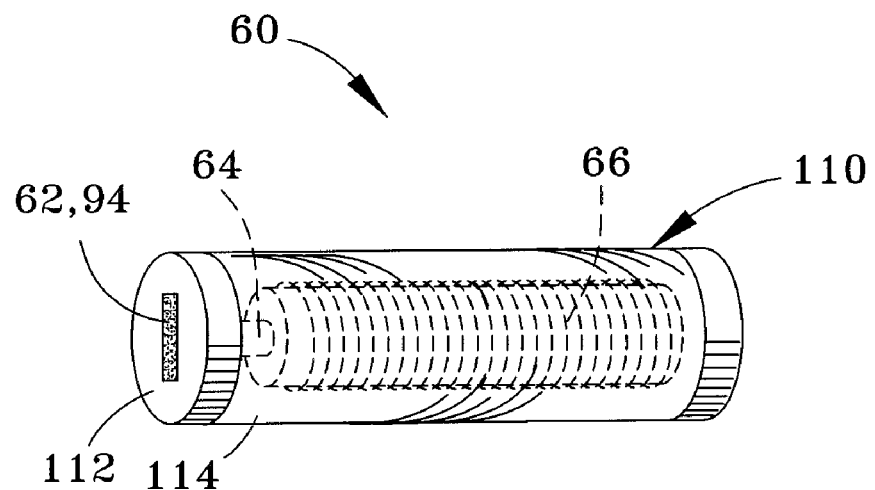

The transducer 62 (e.g., mechanical capacitor 94), the electronic circuitry 64 (including chips, diodes, capacitors, etc., thereof), the antenna 66 and any additional or optional components (e.g., additional transducers 62) of the sensing device 60 (or any alternative sensing device, such as the devices 10 and 30 of FIGS. 1a and 1b) can be contained in a single hermetically-sealed housing. FIG. 4 depicts a preferred example as being a cylindrical housing 110, which is convenient for placing the sensing device 60 within the anchor 120 discussed in reference to FIGS. 5 through 8 below. Other exterior shapes for the housing 110 are also possible to the extent that the exterior shape permits assembly of the sensing device 60 with the anchor 120 as discussed below. The cylindrical-shaped housing 110 of FIG. 4 includes a flat distal face 112, though other shapes are also possible, for example, a torpedo-shape in which the peripheral face 114 of the housing 110 immediately adjacent the distal face 112 is tapered or conical (not shown). The housing 110 can be formed of glass, for example, a borosilicate glass such as Pyrex Glass Brand No 7740 or another suitable material capable of forming a hermetically-sealed enclosure for the electrical components of the sensing device 60. A biocompatible coating, such as a layer of a hydrogel, titanium, nitride, oxide, carbide, silicide, silicone, parylene and/or other polymers, can be deposited on the housing 110 to provide a non-thrombogenic exterior for the biologic environment in which the sensing device 60 will be placed. As can be seen in FIG. 4, the inductive antenna 66 (for example, comprising the coil 68 surrounding the core 70 as represented in FIG. 2a) occupies most of the internal volume of the housing 110. The size of the antenna 66 is governed by the need to couple to a magnetic field to enable telepowering with the readout unit 80 from outside the body, for example, a transmission distance of about ten centimeters or more. The circuitry 64 is disposed between the antenna 66 and the distal face 112 of the housing 110 that preferably carries the transducer 62. A nonlimiting example of an overall size for the housing 110 is about 3.7 mm in diameter and about 16.5 mm in length.

A preferred aspect of the invention is to locate the transducer 62 at or near the distal end of the sensing device 60, for example, the flat distal face 112 of the cylindrical housing 110 or on the peripheral face 114 of the housing 110 immediately adjacent the distal face 112. The distal face 112 can be defined by a biocompatible semiconductor material, such as a heavily boron-doped single-crystalline silicon, in whose outer surface the transducer 62 (for example, a pressure-sensitive diaphragm of the capacitor 94) is formed. In this manner, only the distal face 112 of the housing 110 need be in contact with cerebrospinal fluid, whose pressure (or other physiological parameter) is to be monitored. In the case of monitoring intracranial pressures, this aspect of the invention can be used to minimize the protrusion of the sensing device 60 into the cranial cavity. For example, the sensing device 60 can be placed so that the transducer 62 presses against the dura mater without penetrating the dura mater (extradural), though it is also within the scope of the invention that the sensing device 60 is placed so that the transducer 62 penetrates the dura mater, or the transducer 62 is placed beneath the dura mater (subdural) in the subarachnoid space, or the transducer 62 is placed beneath the pia mater and extends into brain tissue.

Figure 5:
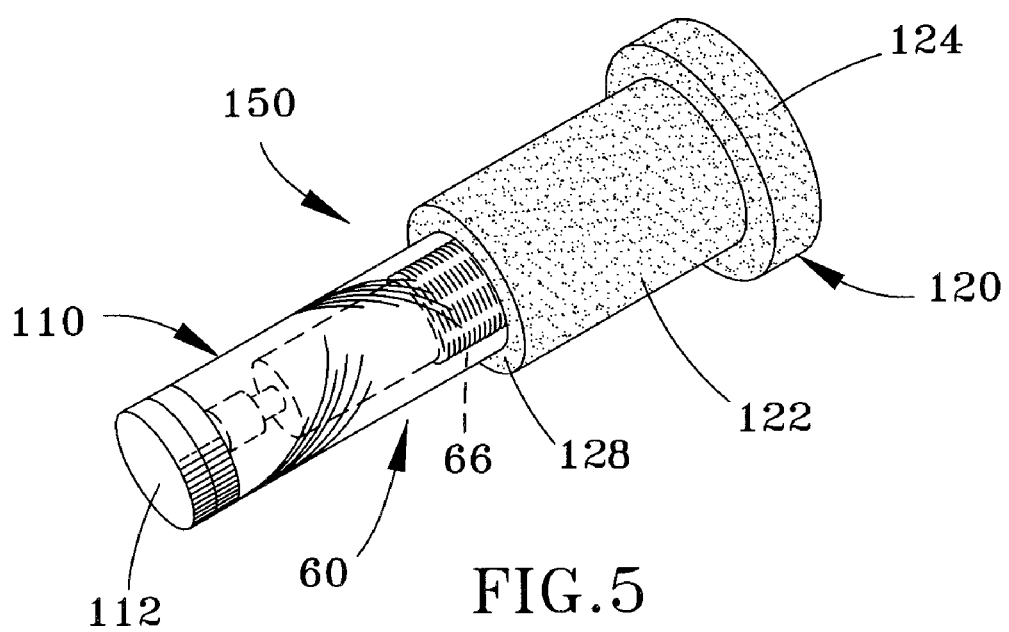
FIG. 5 represents the sensing device of FIG. 4 assembled with an anchor in accordance with a preferred embodiment of the invention.
Figure 6:
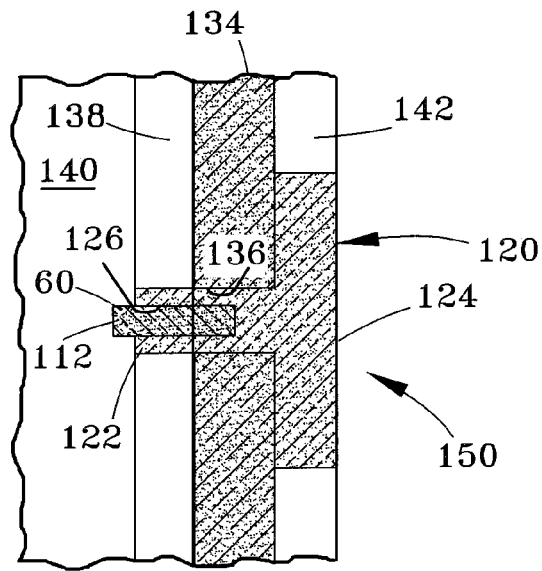
FIGS. 6 through 8 schematically represent sensor units equipped with alternative anchors implanted through a hole in the skull of a subject.

FIGS. 5 through 8 represent different embodiments of the anchor 120 assembled with the sensing device 60 to form the sensor unit 150. In FIG. 5, the sensor unit 150 is represented as a coaxial assembly of the sensing device 60 and anchor 120, with the distal face 112 of the sensing device 60 exposed and the oppositely-disposed proximal end of the sensing device 60 concealed within the anchor 120. As represented in FIG. 6, the sensor unit 150 can be anchored to the skull 134, for example, by making an incision in the scalp 142, drilling a hole 136 in the skull 134, and then inserting the sensor unit 150 in the hole 136 so that the anchor 120 secures the sensing device 60 to the skull 134. The protrusion of the sensor unit 150 and its sensing device 60 relative to the skull 134 can be determined by the anchor 120. For example, the distal end of the unit 150 (for example, as defined by the distal face 112 of the housing 110 or the distal end 128 of the anchor 120) may be slightly recessed or flush with the interior surface of the skull 134 so that the transducer 62 presses against the dura mater 138, or may penetrate into the dura mater 138, or may be placed beneath the dura mater 138 into the subarachnoid space or into brain tissue. As such, the length of the shank portion 122 can be varied depending on the desired location of the transducer 92. Furthermore, the shank portion 122 could be configured as a catheter through which pressure is conducted to the sensing device 60, which can then be located within the shank portion 122 nearer the head portion 124 than the distal end 128 of the anchor 120.

The anchor 120 can be fabricated as a unitary component or as an assembly, and can be formed of various biocompatible materials, nonlimiting examples of which include NITINOL, TEFLON, polymers such as parylene, silicone and PEEK, metals, glass, and ceramics. The anchor 120 is represented in FIGS. 5 through 8 as having a shank portion 122 and a head portion 124 that define, respectively, the distal end 128 and an oppositely-disposed proximal end of the anchor 120. The head portion 124 is represented as having a larger cross-sectional dimension than the shank portion 122 to prevent the entire anchor 120 from being placed within the skull hole 136. The shank and head portions 122 and 124 are represented as having coaxial tubular and disk shapes, respectively, though a round outer periphery is not a requirement for either portion 122 and 124. The shank portion 122 is further represented as having an internal bore 126 that defines an opening at the distal end 128 of the anchor 120. The sensing device 60 is axially disposed within the anchor bore 126 such that the distal face 112 carrying the transducer 62 is exposed outside the anchor 120. The distal face 112 of the sensing device 60 is shown as protruding from the shank portion 122, though it is also within the scope of the invention that the distal face 112 could be recessed within the anchor bore 126. The anchor bore 126 and sensing device housing 110 are represented as having complementary shapes, providing a close fit that prevents biological material (for example, cerebrospinal fluid) from infiltrating the bore 126. The sensing device 60 can be temporarily or permanently secured within the bore 126, for example, with an interference fit or another mechanical securement device, or a biocompatible adhesive such as a cement, glue, epoxy, etc.

Figure 9:
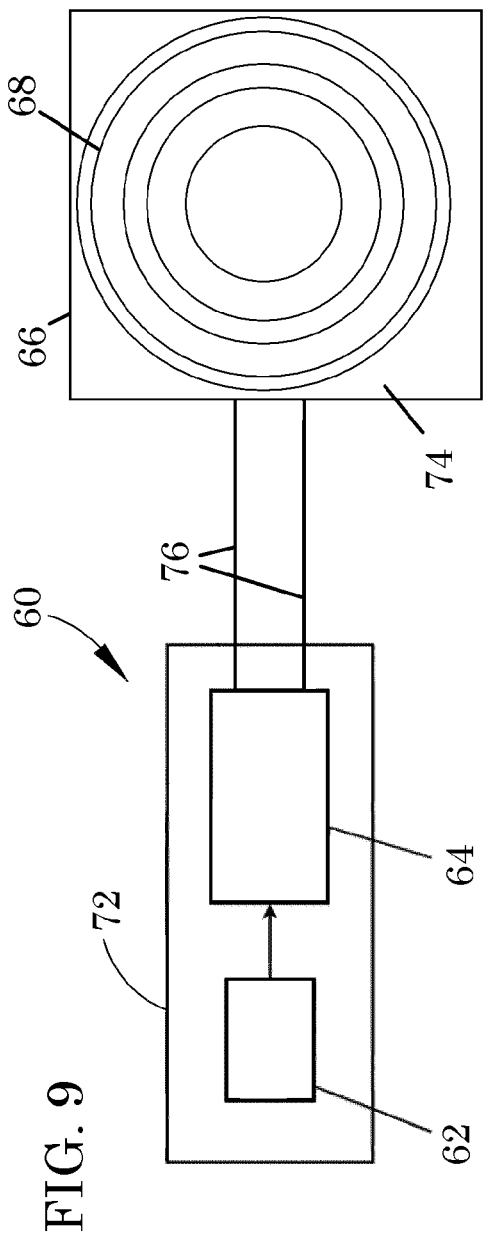
FIGS. 9 and 10 schematically represent, respectively, a sensor unit having a sensing device and a separate antenna subassembly and a sensor unit equipped with a catheter for transmitting a physiological parameter to a transducer within a sensing device, in accordance with additional embodiments of the invention.

While the antenna 66 of the sensing device 60 is shown enclosed with the housing 110 in FIG. 5, the antenna 66 could be placed within the head portion 124 of the anchor 120, or within a separate subassembly placed remotely on the patient and electrically coupled to the remaining components of the sensing device 60 via the anchor 120. As an example, FIG. 9 shows the antenna 66 as a subassembly comprising a flat conductive coil 68 patterned on a substrate 74 and electrically and mechanically connected to a sensor subassembly 72 that includes the transducer 62 and electronic circuitry 64. The subassembly 72 may comprise a housing (similar to the housing 110 of FIGS. 4 and 5) that contains the transducer 62 and circuitry 64, or the subassembly 72 may be formed by potting the transducer 62 and circuitry 64. The antenna and sensor subassemblies 66 and 72 are shown as electrically and mechanically connected with wires 76, though it should be understood that various connections, including rigid, flexible and combinations thereof, are also within the scope of the invention. The wires 76 may be routed through the head portion 124 of the anchor 120 to the antenna subassembly 66, such as through a connector tube (not shown) attached to or forming part of the anchor 120. The antenna subassembly 66, including its substrate 74, conductive coil 68 and any other components, may further include additional electronics, batteries, etc. The coil 68 can be formed using any method known in the art, such as depositing (electroplating, sputtering, evaporating, screen printing, etc.) a conductive material (preferably a highly conductive metal such as silver, copper, gold, etc.) on the substrate 74. The substrate 74 can be formed of a rigid material, a flexible material, or combinations of rigid and flexible materials such as those described above in reference to the substrate for the transducer 62. The substrate 74 is well suited for remote placement from the sensing device 60, such as between the scalp and skull or outside the body on top of the scalp.

In FIG. 6, the sensor unit 150 is represented as anchored to the skull 134, with the shank portion 122 of the anchor 120 received in the skull hole 136, and the distal end of the unit 150 (as defined by the distal face 112 of the housing 110) placed by the anchor 120 beneath the dura mater 138 in the subarachnoid space 140. The head portion 124 of the anchor 120 abuts the exterior surface of the skull 134, and may be exposed through the scalp 142 (as shown) or covered by the scalp 142. The anchor 120 can be secured to the skull 134 with an interference fit between the shank portion 122 and the skull hole 136, and/or with threads formed on the exterior of the shank portion 122, or with a biocompatible cement, glue or epoxy, spring, etc., placed between the skull 134 and the shank portion 122.

Figure 7:
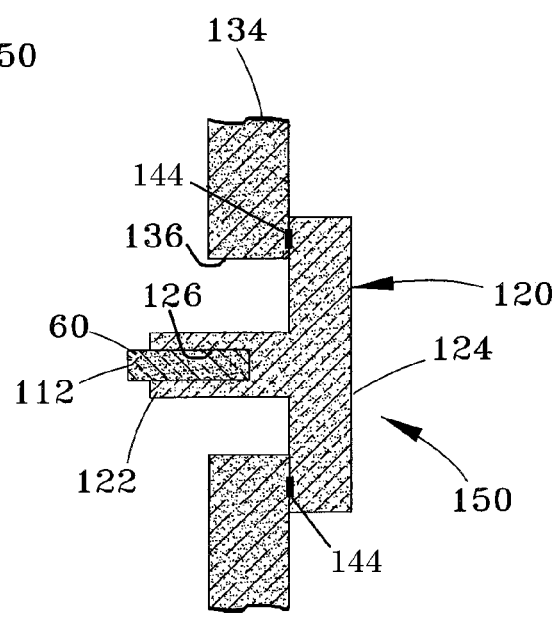

In FIG. 7, the shank portion 122 is shown to have a smaller cross-section than the skull hole 136, for example, as a result of the hole 136 being formed for another medical procedure. The anchor 120 is secured to the skull 134 with the head portion 124 assisted by an attachment element 144, for example, a biocompatible cement, glue or epoxy, screws, nails, etc.

Figure 8:
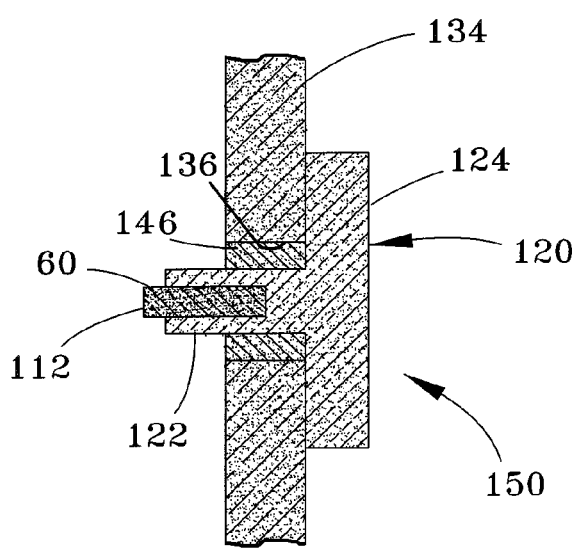

In FIG. 8, the sensor unit 150 is shown as further including an insert 146 between the shank portion 122 and the skull 134. The insert 146 can have a tubular shape, can be secured to the anchor 120 by an interference fit, and can provide for an interference fit with the skull hole 136. Alternatively or in addition, the insert 146 can be or comprise a spring or threads capable of securing the shank portion 122 to the skull 134, optionally assisted by a biocompatible cement, glue or epoxy, nails, etc. A preferred aspect of the embodiment of FIG. 8 is that the anchor 120 is not permanently joined to the insert 146, which permits the insert 146 to remain secured to the skull 134 while allowing the sensor unit 150 and/or its sensing device 60 and/or anchor 120 to be replaced.

In some cases it will be preferred to have a very small minimally-invasive footprint for a pressure sensor when measuring intracranial pressures. In another embodiment of the invention shown in FIG. 10, the sensor unit 150 is represented as further including a small diameter catheter 78 that has a proximal end directly connected to the sensing device 60 and a deformable membrane 79 at its distal tip, which is smaller in diameter than the proximal end. Attachment of the catheter 78 to the sensor unit 150 can be achieved by various methods known to those skilled in the art. For example, biocompatible glues or epoxies, a compression fitting, stitching the catheter 78 to the rim of the sensing device 60 or anchor 120, springs, screws, etc., could be used. The membrane 79 is configured to move in response to pressure, and the catheter 78 contains a pressure-transferring medium, such as a gel, liquid, etc. (not shown), that directly contacts the membrane 79 so that movements of the membrane 79 in response to pressure changes are hydraulically transferred to the transducer 62 located at the distal face 112 of the sensing device 60. Though the unit 150 is represented as utilizing the sensing device 60 with an antenna 66 in close proximity (for example, enclosed in the same housing 110 or potted together) consistent with the embodiments of FIGS. 4 through 8, the unit 150 could make use of a separate antenna subassembly of the type represented in FIG. 9.

Figure 10:
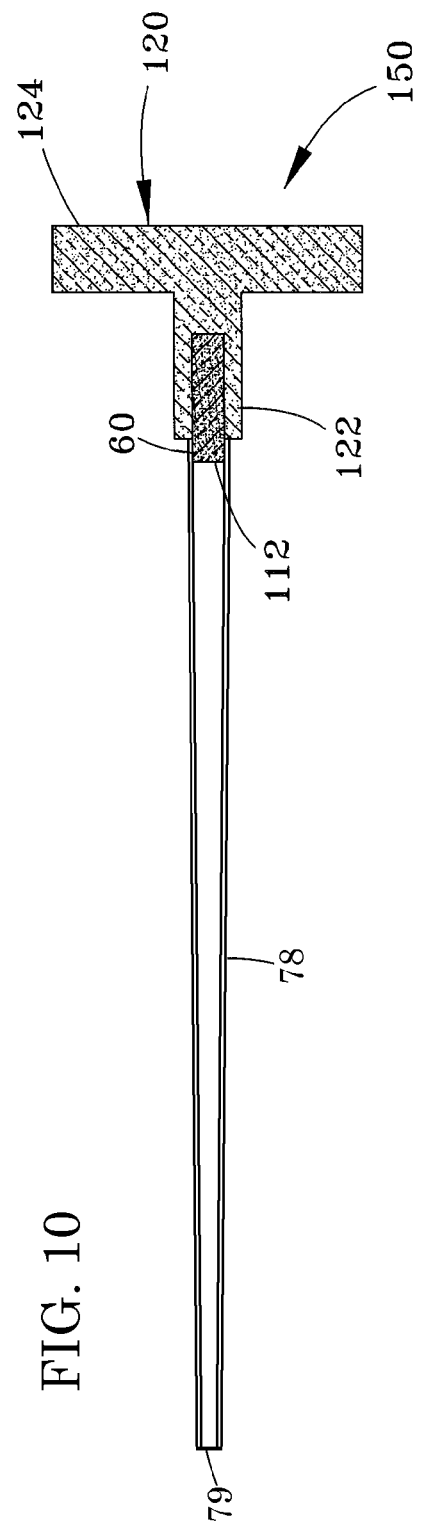

As a result of the construction shown in FIG. 10, only the distal tip of the catheter 78 need be inserted into a region of the body where pressure is to be monitored, enabling a minimally invasive approach that is especially useful for monitoring pressures where space is limited. For example, the catheter 78 is useful in monitoring areas in and around the brain, and particularly within brain tissue, brain ventricle or other areas where a larger footprint could possibly cause damage or be difficult to accurately position.

In all of the embodiments discussed above, one or more sensor units 150 may be simultaneously used in close proximity to each other or in separate locations in the brain. The sensor units 150 may be completely separate units and not share any common elements, generally as represented in FIGS. 5 through 8, or may share a common antenna 66 or other system elements, such as through the use of embodiments based on FIG. 9. In either case, the sensor units 150 can be implanted using minimally invasive outpatient techniques to monitor intracranial pressure. The insertion and placement of the unit 150 is a relatively simple procedure that can be performed by a trained technician, rather than a specialized surgeon. The size and length of the anchor 120 can be varied to accommodate patients of different sizes (both adults and children) and different locations in the brain. By measuring the thickness of the patient's skull and appropriately selecting the length of the shank portion 122 of the anchor 120, the exact location of the transducer 62 at the distal face 112 of the sensing device 60 can be determined by simply inserting the unit 150 within a hole in the skull. This aspect greatly simplifies the exact placement of the transducer 62 and reduces issues/complications relating to placement, movement of the transducer 62 after placement, etc.

In view of the foregoing, it should be understood that a particular use of the sensor unit 150 is to monitor intracranial pressures in patients with traumatic brain injuries (blunt trauma or penetrating trauma), including but not limited to patients with intracranial hemorrhage, closed head injuries, epidural hematoma, subdural hematoma, subarachnoid hemorrhage, diffuse axonal injury, and intracranial hypertension. Depending on the type of injury, the transducer 62 can be implanted into any area of the brain and contact either brain tissue or fluid. In addition to situations involving brain trauma suffered by civilians, the unit 150 can be used for applications including but not limited to situations involving first-responders and in the military. Traumatic brain injury has been identified as the leading cause of death and disability sustained on the battlefield. The unit 150 is capable of significantly improving the quality of treatments received by soldiers in mobile army surgical hospitals, during land and air transportation, and at hospitals, and the mobility of the unit 150 and its separate readout unit 80 allows monitoring to be performed at different stages from battlefield hospital to base hospital to home.

In addition to the above-noted features, the anchor 120 can be modified to provide other functional features useful to the sensing device 60 or sensor unit 150, for example, a device similar to an RFID tag can be added to the anchor 120 to wirelessly transmit ID information concerning the sensing device 60. The ID information may include an ID number, ID name, patient name/ID, calibration coefficients/information, range of operation, date of implantation, valid life of the device (operation life), etc. The anchor 120 may further include additional capabilities such as features for connection to a catheter, shunt, or other device (not shown) that may be useful when monitoring ICP or treating intracranial hypertension (ICH) and severe head injuries.

In addition to the sensing device 60, sensor unit 150 and reader unit 80 described above, the monitoring systems of this invention can be combined with other technologies to achieve additional functionalities. For example, the reader unit 80 can be implemented to have a remote transmission capability, such as home monitoring that may employ telephone, wireless communication, or web-based delivery of information received from the sensor units 150 by the reader unit 80 to a physician or caregiver. In this manner, the reader unit 80 can be adapted for remote monitoring of the patient, closed-loop drug delivery of medications to treat the patient, warning of changes in the physiological parameter (pressure), portable or ambulatory monitoring or diagnosis, monitoring of battery operation, data storage, reporting global positioning coordinates for emergency applications, and communication with other medical devices such as deep brain stimulation (DBS) devices, drug delivery systems, non-drug delivery systems, and wireless medical management systems. Furthermore, the placement of the sensor unit 150 can be utilized as part of a variety of different medical procedures, including diagnosis, treatment intervention, tailoring of medications, disease management, identification of complications, and chronic disease management.

While the invention has been described in terms of specific embodiments, it is apparent that other forms could be adopted by one skilled in the art. As an example, in place of the sensing device 60 of FIGS. 2a and 3 through 10, the implants 10 and 30 of FIGS. 1a and 1b could be used in combination with the anchors 120 and other features depicted in FIGS. 4 through 10. Therefore, the scope of the invention is to be limited only by the following claims.

The invention claimed is:

1. An sensor unit configured to position a sensing element for monitoring a physiological parameter within a cavity of a living body, the sensor unit comprising:
   an anchor comprising:
      a shank portion defining a distal end of the anchor, the shank portion having an outer cross-sectional shape that defines a maximum outer cross-sectional dimension thereof, the shank portion having a bore defining an opening at the distal end of the anchor, the opening having a cross-sectional shape; and
      a head portion defining a proximal end of the anchor and having an outer cross-sectional shape that defines a larger cross-sectional dimension than the maximum outer cross-sectional dimension of the shank portion;
   a sensing device comprising a hermetically-sealed housing that has an outer cross-sectional shape, a proximal end, and an oppositely-disposed distal end at which the sensing element is disposed, the housing containing processing circuitry electrically coupled to the sensing element; and
   a telemetry antennae adapted to communicate with the processing circuitry within the housing of the sensing device;
   wherein the opening in the shank portion of the anchor has a cross-sectional shape that is complementary to the outer cross-sectional shape of the housing of the sensing device, the housing is assembled with the anchor through the opening in the shank portion so that at least the proximal end of the housing is within the bore of the anchor, the distal end of the housing is exposed by the opening of the bore, the housing closes the opening in the bore to prevent biological matter from entering the bore, and the sensing element is exposed by the opening of the bore to sense the physiological parameter.

2. The sensor unit according to claim 1, wherein the shank portion comprises means for securing the anchor within a hole.

3. The sensor unit according to claim 2, wherein the securing means is at least one biocompatible attachment device chosen from the group consisting of inserts, threads, nails, screws, springs, and adhesives.

4. The sensor unit according to claim 2, wherein the anchor consists of the shank portion, the head portion, the bore, and the securing means.

5. The sensor unit according to claim 1 wherein the sensing device is operable to communicate telemetrically a reading of the physiological parameter to a readout device that is not adapted to be implanted in the living body.

6. The sensor unit according to claim 1, wherein the distal end of the housing of the sensing device protrudes from the bore of the anchor such that the sensing device defines a distal end of the sensor unit.

7. The sensor unit according to claim 1 wherein the proximal end of the housing is concealed within the bore of the anchor.

8. The sensor unit according to claim claim 1, wherein the physiological parameter is pressure.

9. The sensor unit according to claim 8, wherein the sensing element comprises a diaphragm responsive to pressure.

10. The sensor unit according to claim 9, wherein the diaphragm is at a distal surface defined by the distal end of the housing of the sensing device.

11. The sensor unit according to claim claim 1, wherein the sensing element comprises a micromachined structure fabricated by additive and subtractive processes performed on a substrate.

12. The sensor unit according to claim 1, wherein the telemetry antenna is adapted for telemetrically communicating a reading of the physiological parameter sensed by the sensing element and electromagnetically receiving power for the sensing device.

13. The sensor unit according to claim 1, wherein the telemetry antenna is within the sensing device.

14. The sensor unit according to claim 1, wherein the telemetry antenna is a separate antenna subassembly and the unit further comprises means for mechanically and electrically coupling the subassembly to the sensing device.

15. The sensor unit according to claim 14, wherein the antenna subassembly comprises a coil on a substrate.

16. The sensor unit according to claim claim 1, wherein the sensor unit is wirelessly coupled with the telemetry antenna to a readout device that is not adapted to be implanted in the living body.

17. The sensor unit according to claim 16, wherein the sensor unit is wirelessly coupled to the readout device for telemetric communication therewith using a resonant scheme in which the sensing device telemetrically receives power from the readout device.

18. The sensor unit according to claim 16, wherein the sensor unit is wirelessly coupled to the readout device for telemetric communication therewith using a passive scheme in which the sensing device telemetrically receives electromagnetic power from the readout device.

19. The sensor unit according to claim 1, wherein the processing circuitry processes electrical communications between the sensing element and the telemetry antenna.

20. The sensor unit according to claim 19, wherein the processing circuitry causes the telemetry antenna to transmit an amplitude modulation transmission.

21. The sensor unit according to claim claim 1, wherein the sensor unit consists of the sensing device, the anchor, and the telemetry antennae.

22. The sensor unit according to claim 1, further comprising a catheter coupled to the housing of the sensing device so that the sensing element of the sensing device is within the catheter, a membrane at a tip of the catheter distal from the sensing device, and means for hydraulically transmitting the physiological parameter from the membrane to the sensing element of the sensing device.

23. A surgical procedure comprising:
providing an anchor comprising a shank portion that defines a distal end of the anchor and a head portion that defines a proximal end of the anchor, the shank portion having a bore defining an opening at the distal end of the anchor, the opening having a cross-sectional shape;
assembling a sensor unit by placing a sensing device through the opening in the distal end of the shank portion of the anchor and into the bore within the shank portion so that the distal end of the anchor or a distal end of the sensing device defines a distal end of the sensor unit, the sensing device closes the opening in the bore to prevent biological matter from entering the bore, and a sensing element of the sensing device is exposed at the distal end of the sensor unit by the opening of the bore, the sensing element being adapted to sense a physiological parameter;
making an incision in the scalp of a patient to expose a portion of the skull;
making a hole through the skull;
placing the shank portion of the anchor the hole such that the distal end of the sensor unit is flush with or protrudes into the cranial cavity within the skull and the head portion of the anchor contacts the skull;
securing the anchor to the skull such that the sensing device is secured to the skull by the anchor and the hole is occluded by the anchor; and then
telemetrically communicating with the sensing device to obtain a reading of the physiological parameter using a readout device located outside the patient.

24. The surgical procedure according to claim 23, wherein, the sensing element is disposed at the distal end of the sensing device, and the distal end of the sensing device protrudes from the distal end of the anchor such that the sensing device defines the distal end of the sensor unit.

25. The surgical procedure according to claim 23, wherein the shank portion occludes the hole as a result of the placing step, and the head portion is not inserted into the hole during the placing step but instead is external to the skull following the placing step.

26. The surgical procedure according to claim 25, wherein the securing step comprises securing the shank portion of the anchor to the skull.

27. The surgical procedure according to claim 26, wherein the shank portion of the anchor is secured within the hole in the skull by an interference fit therebetween.

28. The surgical procedure according to claim 26, wherein the shank portion of the anchor is secured within the hole in the skull by an element chosen from the group consisting of inserts, threads, nails, screws, springs, and adhesives.

29. The surgical procedure according to claim 25, wherein an interference fit does not exist between the shank portion of the anchor and the hole in the skull.

30. The surgical procedure according to claim 25, wherein the securing step comprises securing the head portion of the anchor to the skull.

31. The surgical procedure according to claim 30, wherein the head portion of the anchor is secured to the skull by an element chosen from the group consisting of nails, screws, springs, and adhesives.

32. The surgical procedure according to claim 25, wherein the bore of the anchor is entirely located within the shank portion of the anchor.

33. The surgical procedure according to claim 25, wherein the sensor unit is placed in the hole such that the distal end of the sensor unit presses against the dura mater without penetrating the dura mater (extradural), or penetrates the dura mater, or is placed beneath the dura mater (subdural) in the subarachnoid space, or is placed beneath the pia mater and extends extend into brain tissue.

34. The surgical procedure according to claim 23, wherein the physiological parameter is pressure.

35. The surgical procedure according to claim 23, wherein the telemetric communicating step between the sensing device and the readout device is established using a resonant scheme in which the sensing device telemetrically receives power from the readout device.

36. The surgical procedure according to claim 23, wherein the telemetric communicating step between the sensing device and the readout device is established using a passive scheme in which the sensing device telemetrically receives electromagnetic power from the readout device.

37. The surgical procedure according to claim 23, wherein the sensing device comprises a hermetically-sealed housing that has an outer cross-sectional shape and defines the distal end of the sensing device and an oppositely-disposed proximal end of the sensing device, the procedure further comprising processing electrical communications between the sensing element and a telemetry antenna located within the housing of the sensing device.

38. The surgical procedure according to claim 37, wherein the telemetry antenna is within the housing of the sensing device and is placed with the sensor unit within the hole in the skull.

39. The surgical procedure according to claim 37, wherein the telemetry antenna is a separate antenna subassembly that is not placed with the sensor unit within the hole in the skull.

40. The surgical procedure according to claim 39, wherein the antenna subassembly comprises a coil on a substrate placed outside the skull.

41. The surgical procedure according to claim 37, wherein the telemetry antenna of the sensor unit transmits an amplitude modulation transmission to the readout device.

42. The surgical procedure according to claim 23, wherein the surgical procedure is part of at least one of the following medical procedures: diagnosis, treatment intervention, tailoring of medications, disease management, identification of complications, and chronic disease management.

43. The surgical procedure according to claim 23, wherein the readout device is used to perform at least one of the following:

remote monitoring of the patient, closed-loop drug delivery of medications to treat the patient, warning of changes in the physiological parameter, portable or ambulatory monitoring or diagnosis, monitoring of battery operation, data storage, reporting global positioning coordinates for emergency applications, and communication with other medical devices.

44. The surgical procedure according to claim 23, wherein the sensor unit consists of the sensing device, the anchor, and means for telemetrically communicating the reading of the physiological parameter to the readout device.

45. The surgical procedure according to claim 23, further comprising coupling a catheter to the sensing device so that a membrane at a tip of the catheter is distal from the sensing device, and hydraulically transmitting the physiological parameter from the membrane through the catheter to the sensing element of the sensing device.

46. The surgical procedure according to claim 23, wherein the surgical procedure is performed on the patient in a civilian, military, or mobile army surgical hospital or on a battlefield, or during transportation of the patient therebetween.

\* \* \* \* \*